United States Patent [19]

Shaner

[11] Patent Number: 4,739,754

[45] Date of Patent: Apr. 26, 1988

[54] SUCTION RESISTANT INHALATOR

[76] Inventor: William T. Shaner, 114 Par Dr., Salem, Va. 24153

[21] Appl. No.: 860,299

[22] Filed: May 6, 1986

[51] Int. Cl.[4] .................... A61M 15/00; A61M 15/08; B05D 7/14; B65D 83/06

[52] U.S. Cl. .......................... 128/203.15; 128/203.12; 128/203.23

[58] Field of Search ...................... 128/203.12, 203.15, 128/203.23, 200.17

[56] References Cited

U.S. PATENT DOCUMENTS

| | | | |
|---|---|---|---|
| 16,066 | 11/1856 | Murphy | 128/203.15 |
| 3,795,244 | 3/1974 | Lax et al. | 128/203.15 |
| 4,524,769 | 6/1985 | Wetterlin | 128/203.12 |

FOREIGN PATENT DOCUMENTS 8838 of 1914 United Kingdom ............ 128/203.12

*Primary Examiner*—William E. Kamm
*Assistant Examiner*—George Manuel
*Attorney, Agent, or Firm*—Charles R. Engle

[57] ABSTRACT

A medicinal inhalator utilizing a restriction chamber to mix pressurized medication with air drawn through a filter in a supply duct and to create a flow resistance necessarily causing the medication and air mixture to be drawn into the lungs of the user. The inhalator includes a supply duct which receives a pressurized container of medication, the medication being released upon depression of the container against a surface of a boss formed in the supply duct. The pressurized medication flows through a transmission passage and is mixed with incoming air in a restriction chamber containing a rotating turbine which is in fluid communication with a mouthpiece incorporating a venturi increasing air flow velocity. The restriction chamber can include one or a plurality of rotating turbines in series providing desired predetermined resistance to suction during use of the inhalator.

14 Claims, 2 Drawing Sheets

SUCTION RESISTANT INHALATOR

BACKGROUND OF THE INVENTION

The present invention relates to an inhalator for supplying a medication to a human pulmonary system. More specifically the present invention relates to an inhalator incorporating a predetermined flow resistance to suction forces applied by the user while drawing a medicated air mixture into the pulmonary system of the body. The predetermined resistance necessarily requires the user to breathe extraordinarily deeply conveying the medication more completely throughout the pulmonary system.

Conventional inhalating devices presently used by persons suffering from asthma or other pulmonary conditions do not require an unusually deep breath while inserting a medicinal compound. Consequently oftentimes a shallow breath is drawn and the compound is not given an opportunity to reach all areas of the lung cavities so as to provide maximum effectiveness of the particular medication used. Additionally present devices often result in problems of obtaining a proper mixture with the air during the transmission of the medication to the breathing portions of the body thereby affecting efficiency of the medicinal mixture. An additional problem often incurred with presently used devices is the fact that the medication is not completely drawn out of the inhalating device resulting in undesirable caking and collection of films within the inhalator device.

SUMMARY OF THE INVENTION

The present invention overcomes the problems and disadvantages of the prior art by providing a device which includes means for preventing collection of fluids and films within the interior of the device as well as insuring a minimum suction force which necessarily would be associated with a rather deep breath in order to properly draw the mixture through the inhalating device. These features are accomplished by a simply and efficiently constructed inhalating device that will be later described.

Additional objects and advantages of the invention will be set forth in part in the description which follows, and in part will be obvious from the description, or may be learned by the practice of the invention. The objects and advantages of the invention may be realized and attained by means of the instrumentalities and combinations particularly pointed out in the appended claims.

To achieve the objects and in accordance with the purpose of the invention, as embodied and broadly described herein, the inhalator of this invention comprises a medicinal supply duct having a boss fixed therein, the boss containing a medication transmission passage; a restriction chamber is connected to the supply duct in a substantially normal relationship receiving medication discharged from the transmission passage as it flows axially into the restriction chamber; a container of pressurized medication is received within the supply duct engaging the boss discharging medicant when the container is depressed; at least one turbine rotor is rotatably mounted within the restriction passage receiving the pressurized medicant discharged through the transmission passage, the container is depressed while the user applies suction force drawing air in through an aperture and filter in the supply duct, the flow of the mixture is then restricted by the rotation of the turbine rotor as the user applies suction force to a mouthpiece attached at the downstream end of the restriction chamber; a fixed stator is placed upstream of each turbine rotor directing the pressurized medicant and air mixture into an associated turbine creating a predetermined rotational resistance of the rotor requiring the user to breath deeply insuring that the air-medicant mixture will be deeply drawn into the pulmonary portions of the user; the supply duct being configured to prevent accumulation of discharged medication on the walls and surfaces thereof during use of the inhalator.

The accompanying drawings which are incorporated in and constitute a part of this specification, illustrate one embodiment of the invention and, together with the description, serve to explain the principles of the invention.

DESCRIPTION OF THE PREFERRED EMBODIMENT

Reference will now be made in detail to the present preferred embodiment of the invention, an example of which is illustrated in the accompanying drawings.

Figure 1:
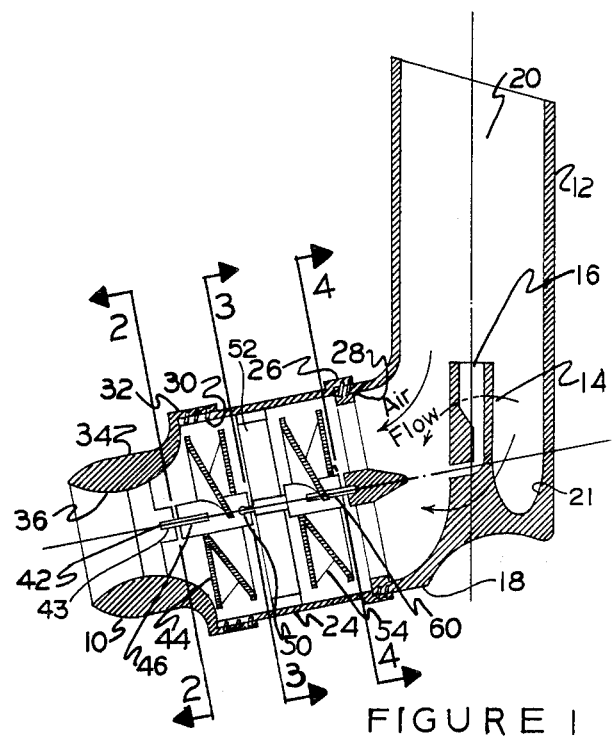
FIG. 1 is a perspective view in section illustrating the elements of the present invention.
Figure 2:
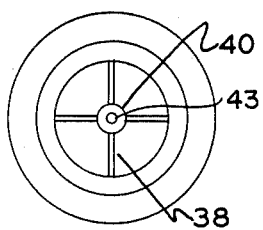
FIG. 2 is a cross-sectional view taken on lines 2—2 of FIG. 1.
Figure 3:
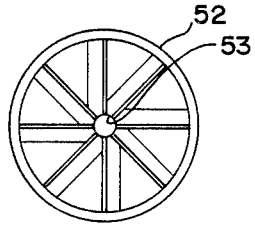
FIG. 3 is a view taken on lines 3—3 of FIG. 1.
Figure 5:
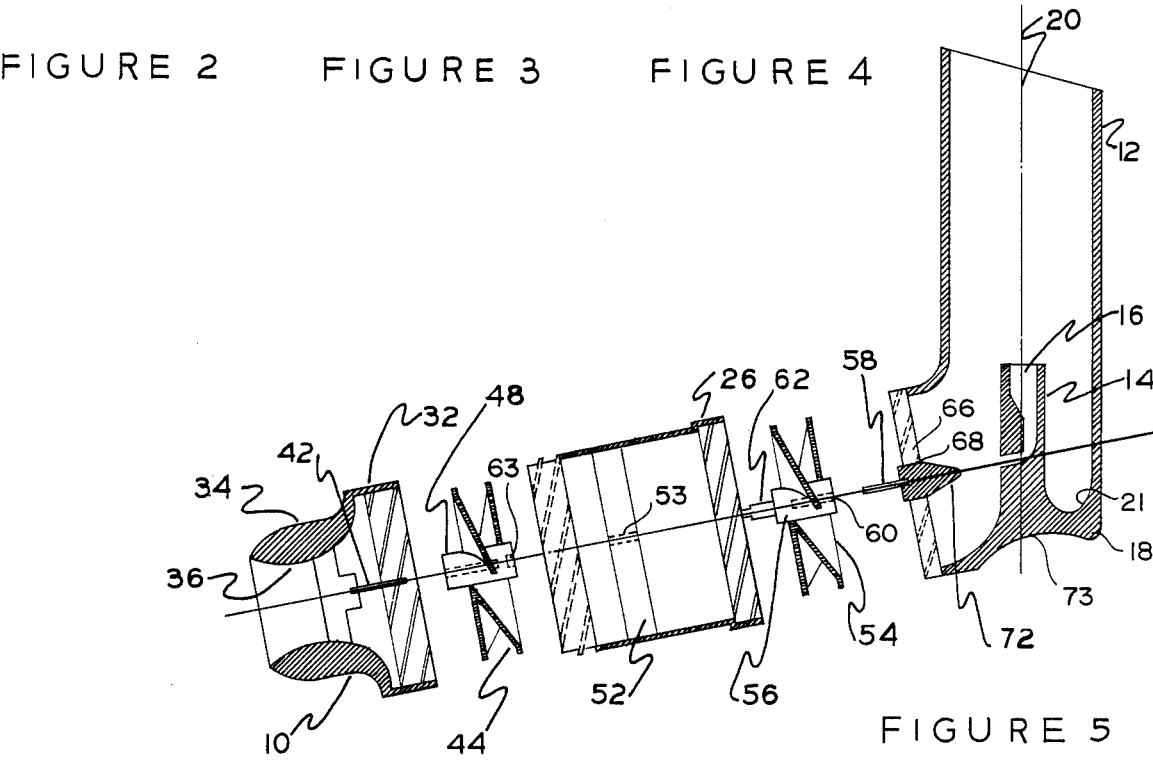
FIG. 5 is an exploded view illustrating the individual components of the present invention.

The preferred embodiment of the suction resistive inhalator is shown in FIG. 1 and is represented generally by the numeral 10. The inhalator includes a supply duct 12 incorporating fixed boss member 14 having a fluid transmission passage 16 formed therein. The supply duct 12 is tubular in shape and is formed to include a fluid directing portion 18 extending substantially normal to a container receiving cavity 20. The cavity 20 is configured to include inner surfaces 21 designed to prevent accumulation of dried and caked medication which would impede fluid flow during subsequent uses of the inhalator. A restriction chamber 24 is connected to portion 18 of supply duct 12 by conventional means. For purposes of illustration, chamber 24 can include a female threaded flange 26 which threadably engages a male threaded portion 28 of portion 18 of supply duct 12. At its downstream end, chamber 24 includes a male threaded portion 30 threadably engaged within a female portion 32 of a mouthpiece 34. The mouthpiece 34 is configured forming a venturi 36, the purpose of which will be described later. As illustrated in FIGS. 2 and 5, the mouthpiece 34 includes a grid 38 providing a central angular bearing number 40 which receives a centering pin 42 in aperture 43 as illustrated in FIG. 1. A downstream rotor 44 is rotatably mounted upon the pin 42 as the pin is received within an aperture 46 in a rotor hub portion 48. The hub portion 48 also receives a pin 50 that is integral with a stator member 52. An upstream rotor 54 includes a hub 56 which receives a pin 58 in a cavity 60 for rotatably supporting the rotor within the resistance chamber 24. The cavity 60 is sized for merely positioning pin 58 such that a minimum of friction resistance to rotation of the pin is created. The hub 56 also includes an extension 62 received within aperture 53 in stator 52 for rotatably supporting the rotor within resistance chamber 24. Aperture 63 receiving extension 62 is also sized for positioning purposes while creating minimal rotational friction.

Figure 4:
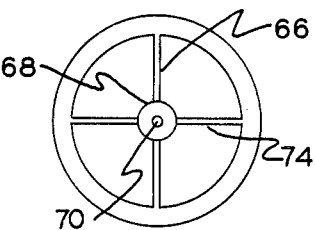
FIG. 4 is a sectional view taken on lines 4—4 of FIG. 1.

As illustrated in FIG. 4, a grid 66 which can be in the form of an inlet stator, includes a centering hub 68 containing a recess 70 receiving rotor supporting pin 58. The hub 68 is tapered at 72 to facilitate airflow through the grid or stator vanes 74 of the grid 66. An arcuate thumb groove 73 is formed in fluid directing portion 18 of supply duct 12 for a purpose later described.

Figure 6:
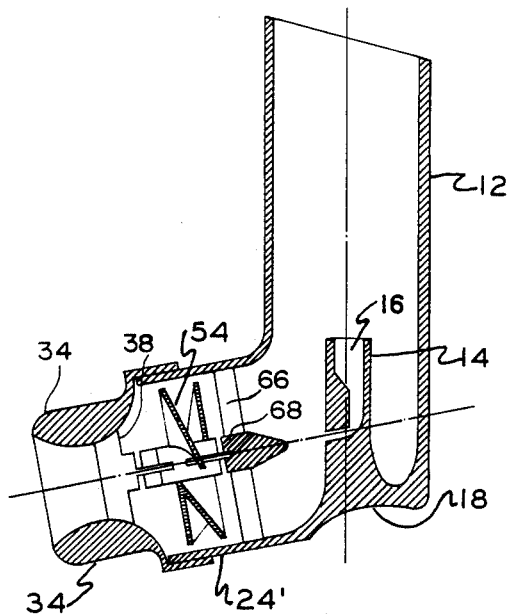
FIG. 6 is a plan view in section illustrating a modification of the present invention.

FIG. 6 discloses a form of the invention utilizing a single impeller 54 providing resistance to flow through the inhalator assembly. Obviously, the impeller 54 can be designed to cooperate with a resistance chamber 24' providing a predetermined desired flow resistance through the inhalator.

Figure 7:
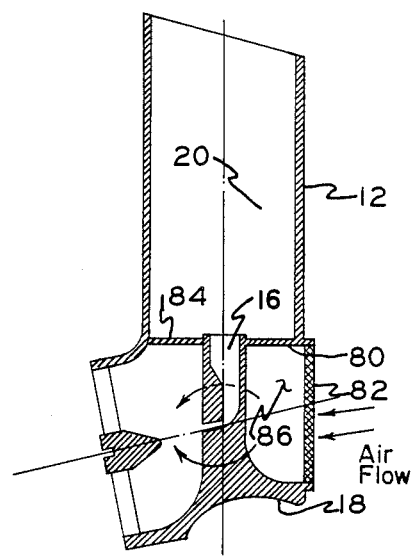
FIG. 7 is a plan view in section illustrating a modification of the supply duct of my invention.
Figure 8:
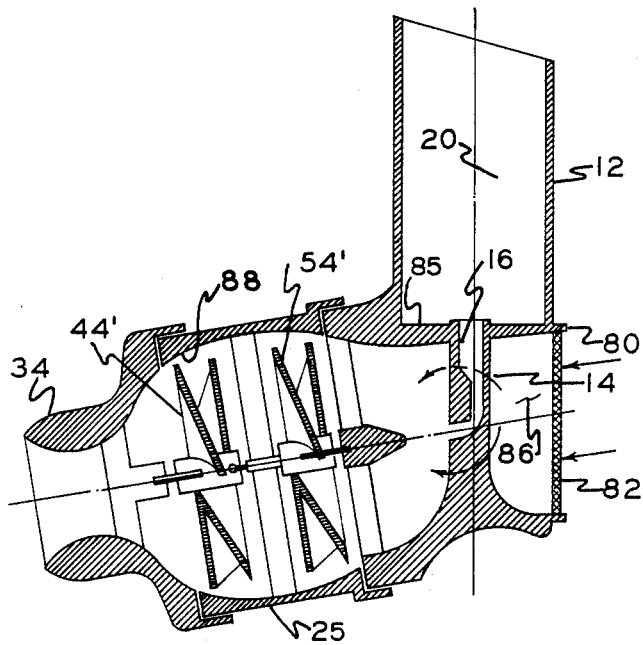
FIG. 8 is a plan view of a further modification of my inhalator assembly.

A modification of the present invention is shown in FIGS. 7 and 8. The supply duct 12 has been modified to include an aperture 80 receiving a removable filter 82 so that air drawn through the aperture 80 for mixing with medication discharged through transmission passage 16 is free of foreign particles prior to entering resistance chamber 25. Supply duct 12 has been further changed to include a wall 84 in FIG. 7 and wall 85 in FIG. 8, sealing chamber 20 from air receiving chamber 86 and in this manner requiring substantially all the air drawn into resistance chamber 24 to pass through the filter 82.

As further illustrated in FIG. 8, restriction chamber 24 is of an enlarged cross-section compared to that of the supply duct 12 and air receiving chamber 86 permitting utilization of enlarged turbine rotors 44' and 54' thereby varying the resistive forces necessary to draw the air-medication mixture through the restriction chamber. From this description it should be readily apparent that the respective diameters of turbine rotors of 44' and 54' can be varied to provide a predetermined resistive force to a suction placed through the mouthpiece 34. A further refinement of the restrictive chamber 24 includes a provision of arcuate surfaces 88 in the terminal portions of the restriction chamber so that the air has a less turbulent and more uniform flow along the interior surfaces of the chamber.

Figure 9:
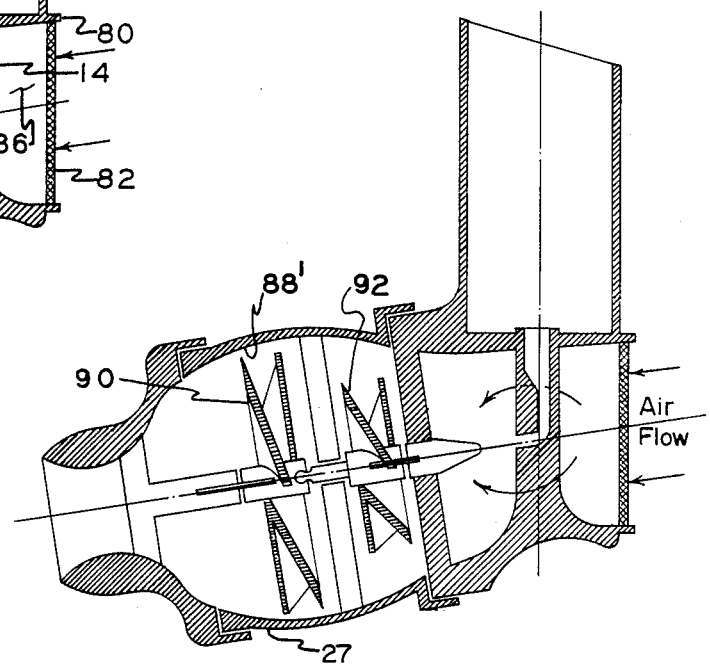
FIG. 9 is a plan view in section of a modified restriction chamber and associated impellers.

FIG. 9 discloses an embodiment with a modified restriction chamber 27 having an inner arcuate surface configured to accommodate impellers 90 and 92 of varying diameters. This arrangement provides means for enhancing mixture of the medication with air and for regulation of flow as the fluid conforms to surface 88'.

In operation the user grasps the inhalator 10 by placing a thumb or finger in arcuate groove 73. Engagement of the thumb in arcuate groove stabilizes the inhalator during depression of a medicinal container in chamber 20. The user then places his or her mouth over the mouthpiece 34 and imparts a suction force to the turbine rotors 44 and 54 rotating them to draw air through aperture 80, shown in FIG. 7 or around the canister placed supply chamber 12. Simultaneously the user will depress the medicinal container against upper surfaces of boss 14 discharging pressurized medication from the container through transmission passage 16 discharging it against conical portion 72 of hub 56 which diffuses the pressurized medication radially outwardly and mixes with air being drawn toward the rotors by suction at mouthpiece 34 through venturi passage 36. The mixed fluid increases in velocity as it is drawn through venturi 36. The rotors 44 and 54 create a predetermined resistive force requiring a predetermined suction by the user which in combination with the increased velocity through venturi 36 assure that the medication will be drawn deeply into the lungs of the user. Additionally the presence of the resistive forces in the restriction chamber 24 require inhalation of a greater volume of medication as well as requiring drawing it deeper into the pulmonary areas of the body. The combination of user suction forces, turbulence of the inhaled fluid generated by the rotors, and the configuration of supply duct inner surfaces 21 cooperating to prevent accumulation of discharged medication on walls and surfaces of the inhalator 10.

It will be apparent to those skilled in the art that various modifications and variations can be made in the suction resistant inhalator of the present invention and in particular the construction of the supply duct in conjunction with the restriction chamber to provide a desired predetermined resistive force to suction applied by the user. Thus it is intended that the present invention cover the modifications and variations of this invention provided they come within the appended claims and their equivalents.

I claim:

1. A medicinal inhalator comprising a medicinal supply duct adapted to receive a pressurized container of medication, said supply duct having inner surfaces designed to prevent accumulation of dried and caked medication interfering with air flow during subsequent use of said inhalator, means in said supply duct supporting said container and being configured to engage said container causing release of medication when said container is depressed against said supporting means, a medication transmitting passage in said supporting means receiving pressurized medication from said container, a restriction chamber having an inlet in fluid communication with said supply duct downstream thereof, impeller means rotatably mounted in said restriction chamber, said impeller means creating a predetermined suction resistance, said medication transmission passage directing pressurized medication into said impeller means, said restriction chamber having an outlet downstream of said impeller means and a mouthpiece including a venturi passage attached to said outlet whereby depressing the medication container against said supporting means discharges medication into said restriction chamber inlet while said impeller creates a resistance requiring a person inhaling to breathe deeply to cause rotation of said impeller and draw air therethrough resulting in transmission of the medication further into the lungs of the user than normally would occur while rotation of said impeller means also more completely mixes the medication with inhaled air.

2. A medicinal inhalator as described in claim 1 wherein said container supporting means is an integral axially projecting boss containing a medication transmitting passage.

3. A medicinal inhalator as described in claim 1 wherein said supply duct extends substantially normal to said restriction chamber.

4. A medicinal inhalator as described in claim 3 wherein said supply duct is provided with an air inlet aperture permitting the suction of air into said restriction chamber as medication is discharged from said container through said transmission passage in said supporting means.

5. A medicinal inhalator as described in claim 4 further comprising of an air filter receiving the air drawn in through said inlet aperture in said supply duct.

6. A medicinal inhalator as described in claim 5 further comprising a wall dividing said medicinal supply duct into a container supporting portion and an air receiving portion preventing air from being drawn in around said container whereby suction on said mouthpiece draws air into said restriction chamber through said filter.

7. A medicinal inhalator as described in claim 1 wherein said supply duct has an arcuate thumb groove in the lower portion thereof for stabilizing said inhalator when grasped by a user with a thumb in said groove.

8. A medicinal inhalator as described in claim 1 wherein said impeller means comprises two impellers serially mounted providing a predetermined desired suction resistance for insuring distribution of medication deeply into the users lungs.

9. A medicinal inhalator as described in claim 8 wherein fixed fluid flow directing stators are provided in said restriction chamber on the inlet side of said impeller rotors.

10. A medicinal inhalator as described in claim 1 wherein said restriction chamber is cross-sectionally enlarged relative to said supply duct providing greater suction resistance and enhanced mixing of air with medication.

11. A medicinal inhalator as described in claim 10 wherein said impeller means comprises two turbine rotors rotatably mounted in series.

12. A medicinal inhalator as described in claim 11 wherein said restriction chamber has turbine stators fixedly positioned directing fluid flow into each of said rotors.

13. A medicinal inhalator as described in claim 12 wherein said restriction chamber further comprises turbine stators fixedly positioned on the outlet side of each said rotors.

14. A medicinal inhalator comprising a supply duct receiving a pressurized container of medication, a supporting boss molded integrally with said supply duct walls and extending axially to said container within said supply duct, said boss containing a transmission passage receiving pressurized medication from said container and discharging it at a predetermined location in said supply duct when depressed against said boss, a restriction chamber of an enlarged cross-sectional area connected to said supply duct in a substantially normal relationship so that said boss transmission passage discharges fluid axially toward said restriction chamber, two turbine rotors rotatably and serially mounted within said restriction chamber, fixed turbine stators mounted within said restriction chamber adjacent each inlet of said turbine rotors, an aperture provided in an exterior wall of said supply duct in axial alignment with said restriction chamber, a wall closing the interior end of said supply duct adjacent said supporting boss preventing suction of air around an installed pressurized medication container, and a mouthpiece secured to the downstream end of said restriction chamber, said mouthpiece containing a venturi increasing the velocity of flow of fluid therethrough whereby said aperture containing said filter and said turbines in said restriction chamber create a predetermined resistance to a mixed fluid exiting said resistance chamber such that the user by necessity must breathe more strenuously than normal, drawing and distributing the medication into the furtherest depths of the lungs.

* * * * *